United States Patent [19]

Sakane

[11] Patent Number: 4,823,801

[45] Date of Patent: Apr. 25, 1989

[54] CORNEA THICKNESS MEASURING ULTRASONIC PROBE

[75] Inventor: Toshio Sakane, Sagamihara, Japan

[73] Assignee: Canon Kabushiki Kaisha, Tokyo, Japan

[21] Appl. No.: 921,009

[22] Filed: Oct. 21, 1986

[30] Foreign Application Priority Data

Nov. 1, 1985 [JP] Japan ............................ 60-245830
Nov. 5, 1985 [JP] Japan ............................ 60-247613

[51] Int. Cl.[4] ........................................... A61B 10/00
[52] U.S. Cl. ........................ 128/661.06; 128/663.01
[58] Field of Search ..................... 128/660, 663, 745; 73/642

[56] References Cited

U.S. PATENT DOCUMENTS

| | | | |
|---|---|---|---|
| 4,183,249 | 1/1980 | Anderson | 73/642 X |
| 4,217,516 | 8/1980 | Iinuma et al. | 128/660 X |
| 4,385,255 | 5/1983 | Yamaguchi et al. | 128/660 X |
| 4,462,092 | 7/1984 | Kawabuchi et al. | 128/660 X |
| 4,484,569 | 11/1984 | Driller et al. | 128/660 |
| 4,570,488 | 2/1986 | Miwa et al. | 128/660 X |
| 4,576,176 | 3/1986 | Myers | 128/660 |

OTHER PUBLICATIONS

Buschmann, W., "New Equipment for Opthalmic Dx", Ultrasonic, Jan.-Mar. 1985, pp. 18-21.

Primary Examiner—Francis Jaworski
Attorney, Agent, or Firm—Fitzpatrick, Cella, Harper & Scinto

[57] ABSTRACT

A cornea thickness measuring ultrasonic probe is provided with an ultrasonic wave propagation layer being in contact with an eye to be examined and formed substantially concentrically with the center of curvature of the cornea of the eye to be examined, a plurality of ultrasonic wave vibrators are disposed on at least one meridian, and a fixation light source is presented to the eye to be examined.

10 Claims, 2 Drawing Sheets

CORNEA THICKNESS MEASURING ULTRASONIC PROBE

BACKGROUND OF THE INVENTION

1. Field of the Invention

This invention relates to a cornea thickness measuring ultrasonic probe for measuring the thickness of the cornea and the distribution thereof by an ultrasonic wave.

2. Related Background Art

Measurement of the thickness of the cornea has been utilized as the monitor of corneal function, and recently it has been used in operations called radial keratotomy, i.e., operations for making myopia into emmetropia by mitigating the curvature of the cornea. In such operations, there is a possibility of injuring the inside spin of the cornea radially and therefore, it is important to adjust the length of the edge of a scalpel and accurately measure the thickness of cornea and the distribution thereof.

The method of measuring the thickness of the cornea may be divided broadly into an optical method and a method using an ultrasonic wave. The optical method can accomplish a generally accurate measurement, but the operation thereof is cumbersome and requires corrections. On the other hand, the method using an ultrasonic wave is simple to handle and can obtain accurate measurement data suitable for use and therefore, is becoming popular.

The probe of an ultrasonic apparatus popular for measurement of an eye includes a single vibrator having a diameter of about 1 mm. To find the distribution of the thickness of the cornea, this probe is moved on the cornea, thereby accomplishing measurement.

This leads to the disadvantages that identification of the measuring position becomes inaccurate and that the tip end of the probe contacting the cornea is small as compared with the diameter of the cornea. Therefore, an unexpected force is exerted on the probe during the movement thereof or during the measurement, which may result in the danger of injuring the cornea. There is also the disadvantage that the thicknesses of the cornea at various positions thereof cannot be properly and stably measured due to the movement of the eyeball including the cornea.

SUMMARY OF THE INVENTION

It is an object of the present invention to provide a cornea thickness measuring ultrasonic probe which can measure the thickness of cornea in at least one meridian direction simply and without injuring the cornea.

It is another object of the present invention to provide a cornea thickness measuring ultrasonic probe which can suppress rotation of the eyeball including the cornea by fixing an eye to be examined and can measure the thickness of the cornea at various positions thereof properly and stably.

It is still another object of the present invention to provide a cornea thickness measuring ultrasonic probe which can effect a warning display when the state of contact thereof with the cornea of an eye to be examined is insufficient.

DESCRIPTION OF THE PREFERRED EMBODIMENTS

Figure 1:
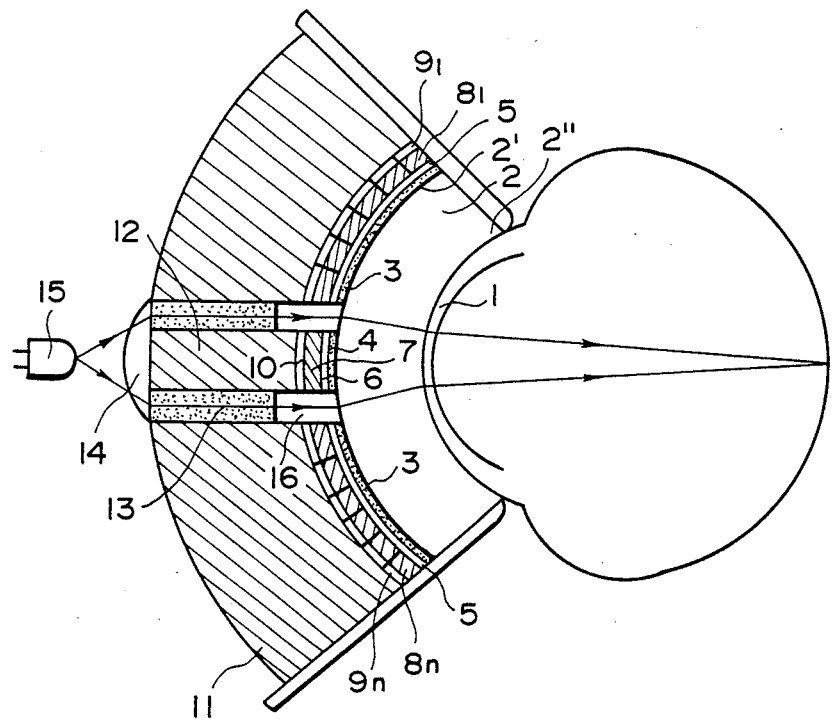
FIG. 1 is a cross-sectional view of an embodiment of the present invention.

FIG. 1 shows an embodiment of the present invention in which a light beam for fixation is projected from between a vibrator for measuring the center thickness of cornea and a vibrator array for measuring the thickness of the marginal portion of cornea.

Reference numeral 1 designates the cornea of an eye to be examined, reference numeral 2 denotes an acoustic propagation layer, reference numerals 3 and 5 designate the acoustic adjustment layer and common electrode of vibrator arrays $8_1, \ldots, 8_n$ for the marginal portion, and reference characters $9_1, \ldots, 9_n$ denote driving electrodes for the vibrator arrays $8_1, \ldots, 8_n$. Reference numerals 4, 6 and 10 designate the acoustic adjustment layer and electrodes of a vibrator 7 for the center. Backing layers 11 and 12, for shortening the acoustic pulse width, are provided behind the vibrator arrays $8_1, \ldots, 8_n$ for the marginal portion and the vibrator 7 for the center. A hollow cylindrical opening layer 16 is provided between the group 3, 5, $8_n$, $9_n$ for measuring the marginal portion and the group 4, 6, 7, 10, 12 for measuring the central portion. A light beam emitted from a light source 15 on the center axis of the probe through said layer 16 are made parallel to the axis of the eye by a lens 14 travels toward the acoustic propagation layer 2 and is projected onto the eye to be examined through the optically transparent acoustic propagation layer 2. A transparent optical member (for example, PMMA: poly-methyl-methacrylate) 13 having parallel end surfaces for holding the backing layer 12 is provided in the cylindrical opening layer 16. The layer 16 between the transparent optical member 13 and the acoustic propagation layer 2 is a layer of a smaller refractive index than the refractive index of the material of the acoustic propagation layer 2, e.g., an air layer. The material of the acoustic propagation layer 2 may be a material which has sufficient acoustic adjustability with the cornea and is optically transparent, such as well-known CR39 or the aforementioned PMMA. PMMA, which is a soft material, is used with a coating for surface reinforcement being applied to the contact surface thereof with the cornea. The optical refractive indices of CR39 and PMMA are of the order of 1.50 to 1.49, while the optical refractive index of the cornea is of the order of 1.38, and when PMMA is simply brought into contact with the cornea, even if a parallel light beam enters the contact surface, the light beam will diverge due to the refraction difference and will not focus on a point on the fundus of the eye and cannot be fixed.

If a light parallel to the axis of the eye is caused to enter an outer peripheral surface 2' of a predetermined curvature to be described substantially concentric with the center of curvature of the cornea through the air layer as the hollow cylindrical opening layer 16, the light beam will focus on a point substantially near the fundus of the eye through three layers whose optical refractive indices are 1, 1.50–1.49 and 1.38, respectively, and sufficient fixation will be obtained. That is, if the layer 16 is air of n=1 and the radius of curvature of the outer peripheral surface 2' of the acoustic propagation layer is about 11.8 mm (thickness being about 4 mm), the point which is in focus will substantially coincide with the fundus of an unadjusted emmetropia.

The above-described members are enclosed in a housing with a lead wire and an extraneous taking-out connector, all not shown, and the appearances thereof are like a contact lens for operation. If the examinee watches the light beam, the measuring position of the vibrator 7 for the center will coincide with the vertex of the cornea and identification of the position with respect to the measuring point will be obtained easily and accurately. That is, by fixing the eye to be examined, rotation of the eyeball including the cornea will be eliminated and the thickness of the cornea at a predetermined position can be measured correctly and stably. The ultrasonic wave is radiated in the direction normal to the outer peripheral surface 2' and perpendicularly enters the inner peripheral surface 2" of the acoustic propagation layer 2, i.e., the surface thereof which is in contact with the cornea, whereby efficient cornea thickness measurement can be accomplished.

Figure 2:
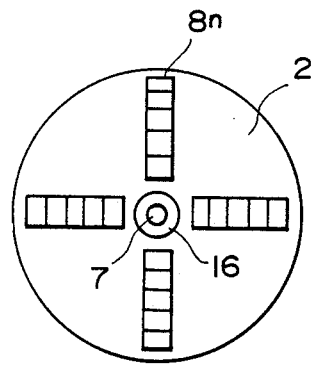
FIGS. 2 and 3 show different embodiments of a fixation system.

After the thickness at the center is thus measured, the vibrator arrays $8_1, \ldots 8_n$ for marginal portion may be electronically scanned and the thicknesses along the meridian may be successively measured. The arrays for the marginal portion may be provided over only a meridian or multiple meridians. FIG. 2 shows an example in which the vibrator arrays for the marginal portion are provided in two meridian directions. Apertures may be formed at the centers of the electrode 10, the vibrator 7 for the center, the electrode 6 and the acoustic adjustment layer 4, and a light beam for fixation may be projected through the apertures.

Figure 3:
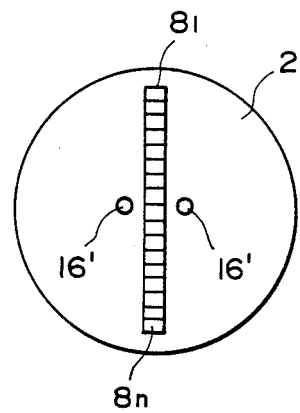

FIG. 3 shows an embodiment in which a vibrator array is provided in a meridian direction and the thicknesses of the cornea in the marginal portion and central portion thereof are measured by the array and the acoustic propagation layer 2 is rotated about the axis of the eye, thereby finding two-dimensional cornea thickness distribution.

In FIG. 3, at the right and left of the central vibrator, two openings 16' for fixation are provided at symmetrical positions with respect to the vibrator and a light beam parallel to the axis of the eye as shown in FIG. 1 is radiated through the air layers of the openings and further through the optically transparent acoustic propagation layer 2.

Figure 4:
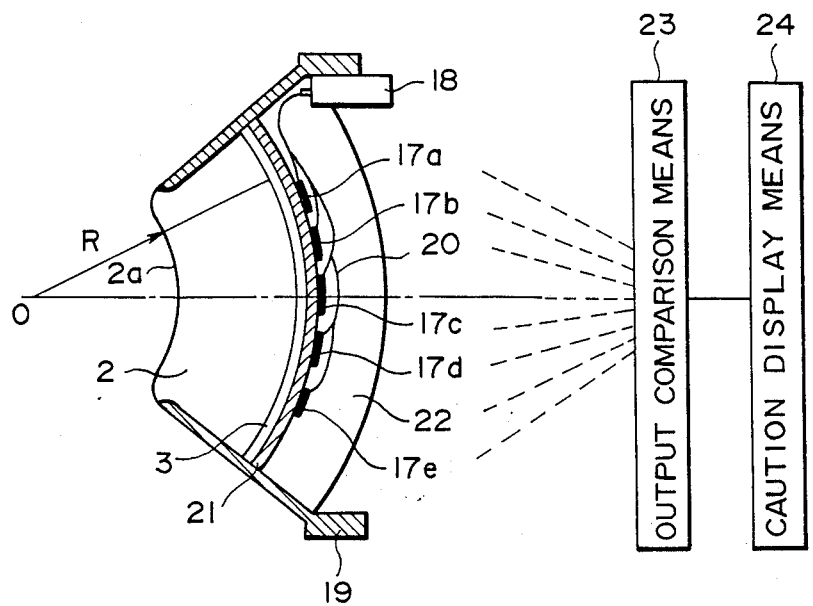
FIG. 4 is a cross-sectional view of a different embodiment of a cornea thickness measuring ultrasonic probe.

FIG. 4 shows an embodiment which is not provided with a fixation system. In FIG. 4, reference numerals similar to those in the aforedescribed embodiment designate similar members.

Figures 5, 6:
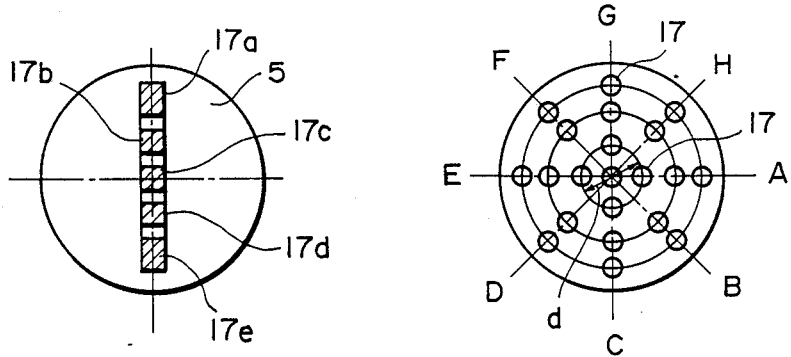
FIGS. 5 and 6 show the arrangement of ultrasonic wave vibrators.

FIG. 4 is a cross-sectional view of a probe the whole of which is shaped like a contact lens for operation. Acoustic adjustment layers 3 and 21 concentric with the center of curvature of cornea are provided within an outer frame 19 formed into a tapered shape, and a delay layer 2 for contacting the cornea of the eye to be examined is provided inside thereof. For example, five ultrasonic wave vibrators 17a-17e are arranged on the outer surface of the adjustment layer 21 along a meridian as shown in FIG. 5, and a backing layer 22 is provided above the vibrators 17a-17e to cover the latter. The outputs of the vibrators 17a-17e are adapted to be connected to an extraneous electrical instrument by a connector 18 through a lead wire 20.

The delay layer 2 is for separating the reflection of the ultrasonic wave from the cornea and the driving pulses for the ultrasonic wave vibrators 17a-17e, and is made, for example, of acryl having substantially the same acoustic impedance as a living body. The acoustic adjustment layers 3 and 21 are layers of a thickness $\lambda/4$ for matching the acoustic impedance of the ultrasonic wave vibrators 17a-17e with that of the delay layer 2, and are formed of a material which will satisfy the relation that $Z0=\sqrt{(Z1 \cdot Z2)}$, where $\lambda$ is the wavelength of the ultrasonic wave, and Z0, Z1 and Z2 are the acoustic impedances of the intermediate layer (Z0) and the layers (Z1, Z2) sandwiching the intermediate layer therebetween.

The ultrasonic wave vibrators 17a-17e are evaporated films formed by evaporating piezoelectric elements having a thickness of $\lambda/2$ which effect thickness vibration of frequency 10-20 MHz, for example, piezoelectric films such as PVDF (polyvinylidene fluoride) or a piezoelectric material such as Cds, and heat-treating and crystallizing the same. Where PVDF is used, the adjustment layers 3 and 21 are unnecessary, but where CdS films are used, the adjustment layers 3 and 21 become important because the acoustic impedance thereof differs from that of the living body by about a unit. In this case, good results may be obtained if, for example, epoxy and $SiO_2$ are used as the adjustment layers 3 and 21, respectively.

Although the electrodes of the ultrasonic wave vibrators 17a-17e are not shown in FIG. 4, if the arrangement of the lead wire 20 as shown in FIG. 4 is adopted, a common electrode may be provided between the adjustment layer 21 and the vibrators 17a-17e and individual electrodes may be provided on that side of the vibrators 17a-17e which is adjacent to the backing layer 22. The backing layer 22 is for providing brake to the vibrators 17a-17e and expediting the absorption of ultrasonic wave, and may preferably be formed of a material such as a mixture of epoxy and rubber which is great in absorption of ultrasonic wave and has a mechanical strength and a great adhesive power.

Now, the adjustment layers 3, 21 and the delay layer 2 are spherical surfaces centered at the center of curvature 0 of the cornea and the delay layer 2 which is the innermost layer is brought into contact with the cornea, but at this time, the ultrasonic wave emitted from the ultrasonic wave vibrators 17a-17e enters the cornea perpendicularly thereto. Further, the radius of curvature of a normal cornea is distributed between 6 mm to 9 mm, but if the radius of curvature of the inner surface 2a of the delay layer 2 is selected to be 7.4-7.8 mm, which is the average value of the distribution of the radius of curvature of the cornea, the difference in radius of curvature will be a minimum and the pressure force for fitting the delay layer 2 to the cornea will be a minimum.

As regards the operation, sterilized distilled water is dripped onto the inner surface 2a of the delay layer 2 and brought into contact with the cornea. A pulse-like ultrasonic wave of the order of 0.3 $\mu s$ is transmitted and received by the use of the vibrator 17c which lies at the center. The thickness is found from the return time of the ultrasonic wave. The vertex of the cornea which is the position at which the thickness is smallest is sought. After the vertex of the cornea has been found, the ultrasonic wave is transmitted and received by the vibrators 17b, 17a, 17d and 17e in succession in accordance with the control by a controller, not shown. The thickness at a fixed position on the same meridian is found, whereby the distribution of the thickness of cornea is found.

When the cornea and the inner surface 2a of the delay layer are not in intimate contact with each other at the marginal portion or the center, the magnitude of the signal output received by the middle vibrator 17c and the magnitudes of the signal outputs received by the vibrators 17a and 17e in the marginal portion are compared by output comparing means 23. Where the difference therebetween exceeds the allowable range, a warning display is effected by a sound or a light from warning display means 24. If the examiner presses the probe in accordance with this warning, he will be able to bring the cornea into intimate contact with the inner surface 2a of the delay layer 2 with the aid of the elasticity provided by eye pressure.

It is apparent that the output comparing means 23 and the warning display means 24 may be provided in the aforedescribed embodiment of FIG. 1.

Now, in the embodiment of FIG. 4, five elements arranged on a meridian as shown in FIG. 5 have been shown as the ultrasonic wave vibrators 17a–17e, and in this case, the thickness distribution on other meridian may be provided by rotating the probe about the center axis by a desired angle and repeating the aforedescribed operation. Alternatively, as shown in FIG. 6, a number of ultrasonic wave vibrators may be arranged on multiple meridians.

When radial keratotomy is the purpose, the thickness on eight meridians A, B, . . . , H shown in FIG. 6 having a diameter of 4 mm or more is required. Where, as shown in FIG. 6, ultrasonic wave vibrators are arranged radially on each of the meridians A, D, . . . H in four rows from the inside including the center, it is considered optimum that the arrangement diameter d of the ultrasonic wave vibrators 17 in the second row is 4 mm and the arrangement diameter of the vibrators 17 in the fourth row is 8-9 mm. The number of rows of the vibrators 17 depends on the diameter of the vibrators 17 and the expanse of the ultrasonic wave beam by frequency and is determined by S/N ratio and resolving power. It is desired to make the thickness of the delay layer 2 as great as allowable and increase the number of rows of the vibrators 17. An increase in the number of rows would pose a problem that the wave transmitting and receiving circuit for driving the vibrators 17 becomes bulky, but compactness of the circuit can be achieved if a driving system is adopted in which the vibrators 17 are divided into a small number of groups within a range in which no cross-talk occurs to the received wave and the transmitted wave is made common in the groups and the received wave is selected for each vibrator 17 by a switch or the like.

What is claimed is:

1. A cornea thickness measuring ultrasonic probe comprising:
    an ultrasonic wave propagation layer having first and second spherical surfaces adapted to be formed substantially concentrically with the center of curvature of the cornea of an eye to be examined, said first surface being adapted to contact the cornea; and
    a plurality of fixed ultrasonic wave vibrators disposed behind said second spherical surface of said ultrasonic wave propagation layer and adapted to be formed substantially concentrically with the center of curvature of the cornea, said vibrators being arranged corresponding to at least one meridian direction of the cornea surface and comprising at least one vibrating element for measuring the thickness of the center portion of the cornea and at least one vibrating element for measuring the thickness of at least one marginal portion of the cornea.

2. A cornea thickness ultrasonic probe according to claim 1, wherein said ultrasonic wave vibrators are adapted to receive driving pulses and transmit ultrasonic waves and receive reflected waves resulting therefrom, and said ultrasonic wave propagation layer comprises a delay layer for separating a reflection of the ultrasonic wave from the cornea and the driving pulses for said ultrasonic wave vibrators, and an acoustic adjustment layer disposed between the respective ultrasonic wave vibrator and the delay layer for matching the acoustic impedance of the ultrasonic wave vibrators and the delay layer.

3. A probe according to claim 1, wherein the radius of curvature of said first surface of said ultrasonic wave propagation layer which is adjacent to the cornea is 7.4–7.8 mm.

4. A probe according to claim 1, wherein said ultrasonic wave vibrators are disposed on a plurality of meridian directions of the cornea surface.

5. A cornea thickness measuring ultrasonic probe comprising:
    an ultrasonic wave propagation layer having first and second curved surfaces adapted to be formed substantially concentrically with the center of curvature of the cornea of an eye to be examined, said first surface being adapted to contact the cornea;
    a plurality of fixed ultrasonic wave vibrators disposed behind said second curved surface of said ultrasonic wave propagation layer and adapted to be formed substantially concentrically with the center of curvature of the cornea, said vibrators being arranged corresponding to at least one meridian direction of the cornea surface and comprising at least one vibrating element for measuring the thickness of the center portion of the cornea and at least one vibrating element for measuring the thickness of at least one marginal portion of the cornea;
    output comparing means for comparing and detecting a difference between the outputs of the at least one vibrating element for measuring the thickness of the center portion of the cornea and the at least one vibrating element for measuring the thickness of the marginal portion of the cornea; and
    warning display means adapted to effect a warning display when the output difference detected by said output comparing means exceeds a predetermined value.

6. A cornea thickness measuring ultrasonic probe comprising:
    an ultrasonic wave propagation layer having first and second curved surfaces adapted to be formed substantially concentrically with the center of curvature of the cornea of an eye to be examined, said first surface being adapted to contact the cornea;
    a plurality of fixed ultrasonic wave vibrators disposed behind said second curved surface of said ultrasonic wave propagation layer and adapted to be formed substantially concentrically with the center of curvature of the cornea, said vibrators being arranged corresponding to at least one meridian direction of the cornea surface and comprising at least one vibrating element for measuring the thickness of the center portion of the cornea and at least one vibrating element for measuring the thickness of at least one marginal portion of the cornea, said ultrasonic wave propagation layer having such optical refractive index and thickness that when a fixed observing light beam coming from a fixation light source presented to the eye to be examined enters into said second curved surface substantially parallel with the axis of the eye through an air layer, said light beam focuses on the fundus of the eye.

7. A cornea thickness measuring ultrasonic probe according to claim 6, further comprising collimating means for collimating light received from the fixation light source located on the axis of the eye.

8. A probe according to claim 6, wherein said fixation light source lies outside said ultrasonic wave propagation layer, and said ultrasonic wave propagation layer is light-transmitting.

9. A cornea thickness measuring ultrasonic probe according to claim 6, wherein said at least one vibrating element for measuring the thickness of the center portion of the cornea includes an outer region for receiving the light beam from the fixation light source.

10. A cornea thickness measuring ultrasonic probe comprising:

an ultrasonic wave propagation layer having first and second curved surfaces adapted to be formed substantially concentrically with the center of curvature of the cornea of an eye to be examined, said first surface being adapted to contact the cornea;

a plurality of fixed ultrasonic wave vibrators disposed behind said second curved surface of said ultrasonic wave propagation layer and adapted to be formed substantially concentrically with the center of curvature of the cornea, said vibrators being arranged corresponding to at least one meridian direction of the cornea surface and comprising at least one vibrating element for measuring the thickness of the center portion of the cornea and at least one vibrating element for measuring the thickness of at least one marginal portion of the cornea; and calculating means for calculating thickness of each portion of the cornea on the basis of the outputs from said at least one vibrating element for measuring the thickness of the center portion of the cornea and said at least one vibrating element for measuring the thickness of the marginal portion of the cornea.

* * * * *